(12) United States Patent
Kjellin (10) Patent No.: US 9,975,772 B2
(45) Date of Patent: May 22, 2018

(54) PRODUCTION OF NANOSIZED CALCIUM PHOSPHATE PARTICLES AS POWDER OR COATING VIA BIFUNCTIONAL PRECURSORS

(75) Inventor: Per Kjellin, Gothenburg (SE)

(73) Assignee: Promimic AB, Gothenburg (SE)

( * ) Notice: Subject to any disclaimer, the term of this patent is extended or adjusted under 35 U.S.C. 154(b) by 966 days.

(21) Appl. No.: 12/744,773

(22) PCT Filed: Nov. 26, 2008

(86) PCT No.: PCT/SE2008/051350
§ 371 (c)(1),
(2), (4) Date: May 26, 2010

(87) PCT Pub. No.: WO2009/070106
PCT Pub. Date: Jun. 4, 2009

(65) Prior Publication Data
US 2011/0282095 A1   Nov. 17, 2011

Related U.S. Application Data

(60) Provisional application No. 60/996,561, filed on Nov. 26, 2007.

(30) Foreign Application Priority Data

Nov. 26, 2007   (SE) ..................... 0702602

(51) Int. Cl.
*C01B 25/32*      (2006.01)
*C23C 24/08*      (2006.01)
(Continued)

(52) U.S. Cl.
CPC ............ *C01B 25/32* (2013.01); *A61K 6/0643* (2013.01); *A61L 27/32* (2013.01); *A61L 27/50* (2013.01);
(Continued)

(58) Field of Classification Search
CPC ......... G11B 5/708; G11B 5/735; G11B 5/738; Y10T 428/12139; Y10T 428/12146
(Continued)

(56) References Cited

U.S. PATENT DOCUMENTS 6,231,607 B1   5/2001   Ben-Bassat et al.
7,169,372 B1   1/2007   Rudin et al.
(Continued)

FOREIGN PATENT DOCUMENTS

| | | |
|---|---|---|
| JP | 2003176111 | 6/2003 |
| JP | 2004155596 | 6/2004 |
| JP | 2006008429 | 1/2006 |

OTHER PUBLICATIONS http://chemistry.about.com/od/imagesclipartstructures/ig/Amino-Acid-Structures/Aspartic-Acid.htm (no date).*
(Continued)

*Primary Examiner* — Samir Shah
(74) *Attorney, Agent, or Firm* — Myers Bigel, P.A.

(57) ABSTRACT

Method of producing calcium phosphate particles, such as hydroxyapatite particles, in the form of a powder or coating on a solid support comprising an oxide surface or a polymer surface, such as titanium, titanium alloys, stainless steel, zirconia, glass and poly(styrene), poly(ether ether ketone) (PEEK), and poly(imide) is described. The method comprises I) providing a water solution containing calcium ions and water-soluble organic compound(s) comprising at least two functional groups, II) providing another water solution containing phosphate ions and water-soluble organic compound(s) comprising at least two functional groups, followed by III) mixing the solutions of (I) and (II) to create calcium phosphate particles coated with said water-soluble organic compounds. After washing and drying, the coated
(Continued)

particles may be used as scaffolds or for production of a powder of calcium phosphate particles or crystals.

12 Claims, 4 Drawing Sheets

(51) Int. Cl.
    *A61L 27/32*     (2006.01)
    *A61L 27/50*     (2006.01)
    *A61K 6/06*     (2006.01)

(52) U.S. Cl.
    CPC ........... *C23C 24/08* (2013.01); *A61L 2420/02* (2013.01); *A61L 2420/06* (2013.01)

(58) Field of Classification Search
    USPC ........................................................ 428/323
    See application file for complete search history.

(56) References Cited

U.S. PATENT DOCUMENTS

| | | |
|---|---|---|
| 2004/0170699 A1 | 9/2004 | Chane-Ching et al. |
| 2005/0158399 A1 | 7/2005 | Yu et al. |
| 2006/0216494 A1* | 9/2006 | Furedi-Milhofer et al. .. 428/323 |
| 2011/0060036 A1* | 3/2011 | Nie et al. ...................... 514/449 |
| 2012/0100121 A1* | 4/2012 | Abribat ........................ 424/94.3 |

OTHER PUBLICATIONS http://www.sigmaaldrich.com/technical-documents/articles/biofiles/poly-lysine.html. (Retrieved on Aug. 31, 2012 ).*
Gonzalez-McQuire, Rosanna et al, "Fabrication of hydroxyapatite sponges by dextran sulphate/amino acid templating", Biomaterials 2005, vol. 26, No. 33, p. 6652-6656, Abstract.

* cited by examiner

PRODUCTION OF NANOSIZED CALCIUM PHOSPHATE PARTICLES AS POWDER OR COATING VIA BIFUNCTIONAL PRECURSORS

The present application is US National Stage of PCT/SE2008/05135 filed Nov. 26, 2008 and claims benefit under 35 U.S.C. 119 (e) of application 60/996,561 filed Nov. 26, 2007, the entire disclosure of which is hereby incorporated by reference.

The current invention relates to production of nanosized calcium phosphate particles as a powder or coating via bifunctional precursors. More precisely, the invention relates to a method of producing calcium phosphate particles, such as hydroxyapatite particles, in the form of a powder or coating on a solid support. The invention also relates to coated calcium phosphate particles in the form of a coating on a solid support comprising an oxide surface or a polymer surface.

BACKGROUND

Biomaterials are materials which are designed to interact with and be incorporated by living tissue. Some examples of biomaterials are dental and orthopaedic implants, surgical sutures and bone cement.

Biomaterials are classified according to their behaviour in vivo. Bioinert materials, such as aluminium oxide, stainless steel, zirconia and poly(ether ether ketone) (PEEK), are compatible with the human body and will not be rejected, but do not promote the integration between the material and the living tissue. Resorbable materials are designed to degrade in vivo and be replaced by living tissue. Resorbable materials include inorganic substances such as calcium sulphate and tricalcium phosphate, but also biodegradable organic polymers. Bioactive materials are said to initiate a biological response which leads to a chemical and biological bond between the material and the living tissue. Hydroxyapatite and so called bioglass are some examples of bioactive materials (1.).

Hydroxyapatite, HA, with the chemical formula $Ca_5(PO_4)_3OH$, is a mineral which closely resembles the calcium phosphate mineral found in bone and teeth. In bone tissue the calcium phosphate crystals exist in the form of rod-shaped crystals with a length of 20-40 nm, 2 nm thick and 2-4 nm wide, surrounded by a collagen network (2.). Due to its bioactive properties, synthetic HA is extensively used in biomaterial applications where an excellent compatibility between the biomaterial and bone tissue is desired. Commercially, synthetic HA is used as an ingredient in bone cements and composite implants, in coatings for dental and orthopaedic implants, and as a bone graft material, among others.

For certain biomaterial applications, it is highly desirable to use nanosized HA with a particle size of 1-100 nm. It is generally considered that the bioactivity of HA is improved if the HA crystals are of a similar size and shape as those produced by the human body. The body recognizes the nanosized HA as a part of its own bone tissue and starts to grow new bone around the foreign object. For implants, a coating with nanosized HA will significantly increase the bone cell activity compared to microsized HA (3.). For HA/polymer composites, the bioactivity as well as the strength is greatly improved with nanosized HA (4.). Syntheses of Nanosized Calcium Phosphates, in Particular HA, in Powder Form.

Synthetic HA is commonly produced by an aqueous precipitation method. This can be done by mixing a soluble calcium salt, such as calcium nitrate, in water together with phosphoric acid, with a Ca/P ratio of 5/3. Crystallization is then induced by raising the pH of the solution, for example with ammonium hydroxide:

$$5Ca(NO_3)_2 + 3H_3PO_4 + 10NH_4OH \rightarrow Ca_5(PO_4)_3OH + 9H_2O + 10NH_4NO_3$$

The immense number of calcium phosphate nuclei which will form immediately after the addition of ammonium hydroxide are typically a few nanometers across. With time, the system will shift toward fewer and larger particles. There are several reasons for this phenomenon. Since the solubility is higher for smaller crystals, there is a tendency for small crystals to dissolve and to crystallize on bigger ones. Small nuclei can also collide and agglomerate to larger crystals, which also results in an average larger crystal size. The driving force is to decrease the overall free surface energy of the system (5.). Due to these effects, a crystallisation done at ambient temperature with calcium nitrate, phosphoric acid and ammonia usually gives a HA powder with a specific surface area of 5-10 $m^2/g$. With a more careful control of the crystallisation parameters, such as pH, concentration, precursor salts, temperature and aging time, it is possible to achieve HA powder with specific surface areas between 40-60 $m^2/g$. The crystal size can also be decreased further by grinding, whereby the crystals are crushed to even smaller sizes (6.).

With additives present in the crystallising solution it is possible to alter the crystallisation process. Additives can adsorb to the crystal surface and prevent dissolution of small crystals, and also shield the crystals from colliding. These effects can shift the crystal size distribution towards smaller crystals. Additives, such as for example poly (ethylene glycol) (7.) and ethanol (8.) have been shown to affect the crystal growth of HA.

Surfactants can also be used as crystal growth inhibitors, since they adsorb on surfaces and therefore can stabilize small crystals. Using surfactant self-assembly methods, it is possible to obtain high specific surface areas of HA. A microemulsion is one example of a self-assembling surfactant system, consisting of nanometer-sized surfactant spheres with water on the inside and a hydrophobic solvent on the outside. When crystallisation is initiated inside the water domains, the microemulsion droplets act as uniformly sized reaction vessels, which protect the precipitated crystal nuclei from further agglomeration and thus yield crystals in the nanometer range (9.).

Bose et al. describes a method to synthesize hydroxyapatite with micro-emulsions, giving a hydroxyapatite powder with a specific surface area of 130 $m^2/g$ (10.).

Depending on the surfactant type, other self-assembly structures may form, such as liquid crystalline phases. A liquid crystalline phase is a self-assembly structure which can be created with high concentration ratios of surfactant/water. Compared to a microemulsion, a liquid crystalline phase is a more rigid structure which more effectively will prevent the aqueous domains from colliding. Using liquid crystalline phases it is possible to synthesize HA crystals with a specific surface area of 150-300 $m^2/g$ (11.) Additives, such as stearic acid, in combination with synthesis in liquid crystalline phases has also been examined. If stearic acid is present in the water domains of the liquid crystalline phase, the carboxylate group will adhere to the surface of the HA crystals and thereby prevent the crystals from agglomeration. The result is a powder with HA crystals encapsulated by a layer of stearic acid. Upon heat treatment this produces a HA powder of calcium carbonate encapsulated HA crystals. (12.).

The main disadvantage with the methods based on surfactant self-assembly is the relatively low yield. The weight ratio of surfactant/HA crystals is often 100/1. This makes large scale synthesis of nanocrystalline HA powder a cumbersome process, since extensive filtering equipment is needed to purify the crystals and the surfactants used in the process has to be taken care of. There is thus a demand for methods that makes it possible to efficiently produce nanosized crystals of HA.

Syntheses of Nanosized Calcium Phosphates, in Particular HA, as Coatings.

There exists a number of methods to coat implants with HA. The plasma spray technique for example, uses high temperatures to evaporate a HA layer on the implant. The result is a relatively thick layer, usually 60-80 µm, of calcium phosphate which adheres strongly to the substrate (13.). Due to the high temperatures in the plasma, as high as 30 000° C., the calcium phosphate has a high amorphous content (14.). This technique produces uneven coatings on porous implants, and with such a thick layer of HA it is not possible to retain the original surface structure of the substrate.

With the sol-gel technique it is possible to use wet application methods, such as dip-coating, to apply a thin layer of calcium phosphate on implant surfaces. However, this technique requires high temperatures, usually approximately 800° C., or long exposure times at such elevated temperatures to obtain a high crystallinity of the HA layer and is therefore unsuitable to use on titanium implants. It is possible to obtain a thin layer with a Simulated Body Fluid (SBF) immersion technique, wherein the implant is immersed in a SBF for a prolonged period, during which HA crystallizes on the implant surface (15.) The SBF technique works at room temperature but demands long exposure times (at least 24 hours) for a stable HA layer to precipitate on the surface.

The surfactant mediated technique described in EP1781568 (11.) makes it possible to coat the implants with a very thin (5-10 nm) layer of calcium phosphate. The heat treatment step is performed at 500° C. for 5 minutes. This temperature is needed to ensure the decomposition of remaining surfactants on the substrate.

Nishimura et al. (16.) describe a two-step technique to coat surfaces with HA nanocrystals. The substrate is initially coated with an alkoxide, such as aminopropyl-trimethoxysilane. Subsequently, the substrate is dipped into a solution of nanocrystalline HA particles, which creates a layer of HA particles on the surface. The disadvantage with this method is the two-step procedure wherein the substrate must be treated with an alkoxide prior to the attachment of the HA crystals. There is a demand for a one-step method of coating a solid surface with HA nanoparticles.

Surface-Modified HA Crystals.

As already mentioned, a powder with HA crystals encapsulated by a layer of stearic acid has been produced, which upon heat treatment gave a HA powder of calcium carbonate encapsulated HA crystals. (12.).

Stupp et al (17.) describe a technique to adhere polymerized amino acids such as poly(L-lysine), to calcium phosphate crystals. The poly(amino acid)-calcium phosphate aggregates are then attached to a metal surface which has previously been seeded with a layer of calcium phosphate crystals. The result is a layer, usually in the micrometer range, of calcium phosphate crystals dispersed in a network of poly(amino acid) fibers. The average size of the individual crystals is 100-500 nm.

Gonzalez-McQuire et al. (18.) describe a technique to produce HA with attached amino acids. The crystallisation is done by mixing $Ca(NO_3)_2$, ammonium phosphate and amino acid with molar ratios of Ca:P:amino acid of 3:1:6 at pH 9 and at a temperature of 80° C. This method creates agglomerated nanosized surface-modified HA crystals.

However, technical solutions are still sought for the need to find techniques to produce nanosized calcium phosphate particles and crystals that have better feasibility and provide HA particles of a small size and high specific surface area.

DESCRIPTION OF THE INVENTION

The current invention provides production of nanosized calcium phosphate particles as a powder or coating on a solid support comprising an oxide surface or a polymer surface via bifunctional precursors, by which the above-mentioned problems are overcome. The present invention also provides precursors, i.e. calcium phosphate particles comprising a coating of water-soluble organic compound(s) comprising at least two functional groups.

By the use of a bifunctional molecule, it is possible to tailor-make the calcium phosphate particles or crystals with different coatings on the particle or crystal surface. In particular, it is desirable to have one end of the molecule attached to the surface of the calcium phosphate particle or crystal, and the other end of the molecule facing the solution. The part of the molecule facing the solution will prevent the crystals from colliding and stop further growth. The nanosized particles or crystals can then be filtered and heated to remove the organic molecules. The heating of the particles or crystals should be to a temperature high enough to burn away the organic part but lower than the temperature at which a phase transformation occurs. Particle or crystal agglomeration can also be prevented if molecules with a positive or negative charge are attached to the particle or crystal surface. The particle or crystal surfaces will then have a strongly negative or positive charge and will repel each other by so-called electrostatic repulsion.

As the coating on the calcium phosphate particles or crystals have a positive charge, it is possible to attach them to a negatively charged surface. Modifying the surface of the calcium phosphate particles or crystals in this way will create a net positive charge on the particles or crystals, making it possible to attach these on negatively charged surfaces. Examples of surfaces which have a negative charge in an aqueous solution of pH of approximately 7 include metals such as titanium, titanium alloys, titanium-aluminium-vanadium and stainless steel, ceramics such as zirconia and glass, and also polymers such as poly(styrene) (19) and poly(ether ether kethone) (PEEK) (20). Polymers as solid support have a polymer surface; the solid support may consist entirely of a homo-polymer or a co-polymer. Alternatively, a metal may be coated with a homo-polymer or co-polymer. The solid support may be an implant, and may further comprise a surface for supporting the growth of e.g. bone cells.

When the modified calcium phosphate particles or crystals have been allowed to attach on the negatively charged surface, then the bifunctional molecules can be removed from the surface by heating. Thus, the solution with surface modified calcium phosphate particles or crystals can be used to produce nanosized particles or crystals by filtering, drying and heating the particles or crystals, but the solution may also be used as a coating solution for various surfaces. Since the modified calcium phosphate particles attach to the surface electrostatically, omitting the heating step will create a coating consisting of coated calcium phosphate particles or crystals.

There are a number of different molecules which may serve the purpose of attaching one end to the HA particle or crystal and letting the other end face the solution. Examples of functional groups that may attach to the HA crystal surface include —COOH, —OPO$_3$H$_2$ and —OSO$_3$H groups. An example of a positively charged functional group that may be facing the solution include —NH$_2$.

An example of a bifunctional molecule useful in the current invention is gamma-amino butyric acid (GABA) that has a carboxylic acid group in one end and an amino group in the other. If GABA is present during the crystallisation of HA, the carboxylic acid end may attach to the calcium ions on the surface of the crystal, with the amino end facing the solution. 6-Aminohexanoic acid is another example of a similar amino acid with a longer carbon chain. If subjected to heating, the amino acids are considerably less stable than for example linear carboxylic acids, which makes it possible to remove them at temperatures as low as 200-250° C. Being able to remove the molecules at low temperatures is important in order to preserve a small particle size and a high specific surface area of the HA powder. A low temperature removal of the organic molecules is also important when applying the nanocrystalline HA as a coating on implant surfaces which are sensitive to oxidation, such as titanium. Alternatively, the heating step may be omitted and excess amino acids may be removed by washing, extraction or filtering, creating a coating consisting of coated calcium phosphate particles or crystals. Omitting the heating step may be desirable when coating polymers which melt at low temperatures, such as poly(styrene). This makes it possible to apply the coating on polymer-based cell culture supports, such as petri dishes and multi-well plates, which can be useful in the cultivation of for example bone cells.

The crystallisation process is undertaken in such a way that an aqueous phosphoric acid solution is reacted with GABA in a molar ratio of GABA:H$_3$PO$_4$ equal to 3:1. The amino group neutralizes the phosphoric acid according to:

$$3NH_2(CH_2)_3COOH+H_3PO_4 \rightarrow [NH_3(CH_2)_3COOH]_3PO_4$$

The calcium solution is prepared by reacting an aqueous solution of calcium oxide or calcium hydroxide with GABA, which is written as:

$$2NH_2(CH_2)_3COOH+Ca(OH)_2 \rightarrow Ca[NH_2(CH_2)_3COO]_2+2H_2O$$

The two solutions are subsequently mixed, which is written as:

$$5Ca[NH_2(CH_2)_3COO]_2+3[NH_3(CH_2)_3COOH]_3PO_4+H_2O \rightarrow Ca_5(PO_4)_3OH+19NH_2(CH_2)_3COOH.$$

Thus, one aspect of the invention is directed to a method of producing calcium phosphate particles in the form of a powder or coating on a solid support comprising an oxide surface or a polymer surface, comprising:
I) providing a first water solution containing calcium ions and water-soluble organic compound(s) comprising at least two functional groups, wherein at least one of the functional groups is a negatively charged group and at least one is a positively charged group,
II) providing a second water solution containing phosphate ions and water-soluble organic compound(s) comprising at least two functional groups wherein at least one of the functional groups is a negatively charged group and at least one is a positively charged group,
III) mixing the solutions of (I) and (II) at ambient temperature to create calcium phosphate particles coated with the water-soluble organic compounds via the negatively charged groups, the pH being neutral or basic in the resulting mixture, followed by either
IV) extracting the formed calcium phosphate particles coated with the organic compounds from the mixture of (III) and washing of the coated particles, followed by drying to produce a powder of the calcium phosphate particles coated with the organic compounds; and
V) removing the organic compounds by heating at a temperature in the range of 250° C.-600° C. to produce a powder of calcium phosphate particles, or
VI) immersing a solid support comprising an oxide surface or a polymer surface into the mixture of III) whereby the positively charged groups of the organic compounds coating the calcium phosphate particles attach to the solid support, followed by removing the solid support from the mixture and allowing the solid support attached to the calcium phosphate particles coated with the organic compounds to dry, followed by either
VII) Removing excess amounts of the organic compounds to form a coating of coated calcium phosphate particles on the solid support,
or
VIII) removing the organic compounds by heating at a temperature in the range of 200° C.-600° C. to form a coating of calcium phosphate particles on the solid support.

"Removing excess amounts of the organic compounds" is defined herein as removal by way of washing, extraction or filtering, whereby the heating step is omitted. Thereby, organic compounds forming part of the coated calcium phosphate particles are not removed therefrom.

Examples of the heating temperature in the range of 250° C.-600° C. in step V) are any temperatures selected form the rages of temperatures from 250° C. to 300° C., to 350° C., to 400° C., to 450° C., to 500° C., or to 550° C., such as from 300° C. to 500° C., for example approximately 400° C.

Examples of the heating temperature in the range of 200° C.-600° C. in step VII) are any temperatures selected form the ranges of temperatures from 200° C. to 250° C., to 300° C., to 350° C., to 400° C., to 450° C., to 500° C., or to 550° C., such as from 200° C. to 500° C., or from 250° C. to 450° C., for example approximately 400° C.

The water-soluble organic compound(s) comprising at least two functional groups, wherein at least one of the functional groups is a negatively charged group and at least one is a positively charged group in I) and II) may be the same or different compounds, and may be mixtures of two or more individually selected such water-soluble organic compounds.

The term "water-soluble organic compound" as used in this specification and in the claims refers to an organic compound that is soluble in water to such extent that it can function in the method of the invention. The more water-soluble the organic compounds used in the invention are, the higher concentrations thereof in water are possible and the higher yields of the final products will be obtained.

In an embodiment of the invention, the calcium phosphate particles are in crystalline form.

In another embodiment of the invention, the negatively charged groups of the organic compounds are selected from the group comprising —COOH, —OPO$_3$H$_2$ and —OSO$_3$H groups, and the positively charged groups of the organic compounds are amine groups.

In a further preferred embodiment of the invention the calcium phosphate particles are hydroxyapatite.

Thus, by use of the method of the invention, hydroxyapatite with a Ca/P ratio of 1.67 is obtained, which is the ratio of naturally occurring hydroxyapatite. However, other phosphate compounds may be produced according to the invention by altering the ratio of the compounds generating calcium and phosphor ions in water, such as dicalcium phosphate or octacalcium phosphate.

Examples of compounds generating phosphor ions in water include phosphoric acid, phosphorous acid, hypophosphorous acid and phosphorous acid esters, such as triethyl phosphite.

Examples of compounds generating calcium ions in water include calcium oxide, calcium hydroxide, calcium carbonate, calcium nitrate, calcium chloride, calcium acetate, and calcium alkoxides such as calcium ethoxide.

In yet another embodiment of the invention, the organic compound(s) in I) and/or II) is (are) selected from water-soluble organic compounds with three functional groups, e.g. lysine.

In still another embodiment of the invention, the organic compound(s) in I) and/or II) is (are) selected from the group consisting of neutral amino acids, basic amino acids, and acidic amino acids. Thus, apart from using neutral amino acids with an equal number of amine and carboxylic acid groups, it is also possible to use basic amino acids such as lysine, and acidic amino acids such as aspartic acid.

In a further embodiment of the invention, the solid support comprising an oxide surface or a polymer surface to which the coating is attached is selected from titanium, titanium alloys, stainless steel, zirconia, glass, poly(styrene), poly(ether ether ketone) (PEEK), and poly(imide)

In an embodiment of the invention, the solid support is an implant, such as a dental implant. In another embodiment of the invention, the solid support is a cell cultivating support, such as a petri dish.

Another aspect of the invention is directed to coated calcium phosphate particles in the form of a powder or a coating on a solid support comprising an oxide surface or a polymer surface, the particles comprising a coating of water-soluble organic compound(s) comprising at least two functional groups, wherein at least one of the functional groups is a negatively charged group and at least one is a positively charged group, and the organic compound(s) is (are) attached to the calcium phosphate particles via the negatively charged groups and the positively charged groups of the organic compound(s) coating the calcium phosphate particles attach to the solid support. Such coated calcium phosphate particles are in an embodiment of the invention in crystalline form. The coated particles or crystals are useful in production of the calcium phosphate particles or crystals in the form of a powder or coating according to the invention when the organic molecules are removed by for example heating or washing. The particles or crystals may also be used e.g. as scaffolds for cell growth.

Also this aspect of the invention embraces the embodiments mentioned in connection with the method aspect of the invention, i.e. embodiments wherein the negatively charged groups are selected from the group comprising —COOH, —OPO$_3$H$_2$ and —OSO$_3$H groups and the positively charged groups are amine groups, wherein the calcium phosphate is hydroxyapatite, wherein the organic compounds are selected from water-soluble organic compounds with three functional groups, and wherein the organic compounds are selected from the group consisting of neutral amino acids, basic amino acids and acidic amino acids.

The invention will now be illustrated with reference to Examples and the Drawings, but it should be understood that the scope of the invention is not limited to the disclosed details.

EXAMPLES

Example 1

A) In a typical experiment, 10.4 g of gamma-amino butyric acid (GABA) was dissolved in 150 ml H$_2$O. 2.82 g of CaO was added to the solution and allowed to stir for 10 minutes. This solution had a pH of 11.7. Solution 2 was prepared by adding 9.3 g GABA to 150 ml H$_2$O. 3.45 g of H$_3$PO$_4$ was added to this solution and allowed to stir for 10 minutes. This solution had a pH of 4.50. Solution 1 was subsequently mixed with solution 2, and a crystallisation resulted. The crystallisation was carried out at ambient temperature, and the pH of this mixture was measured to 9.12.

Figure 2:
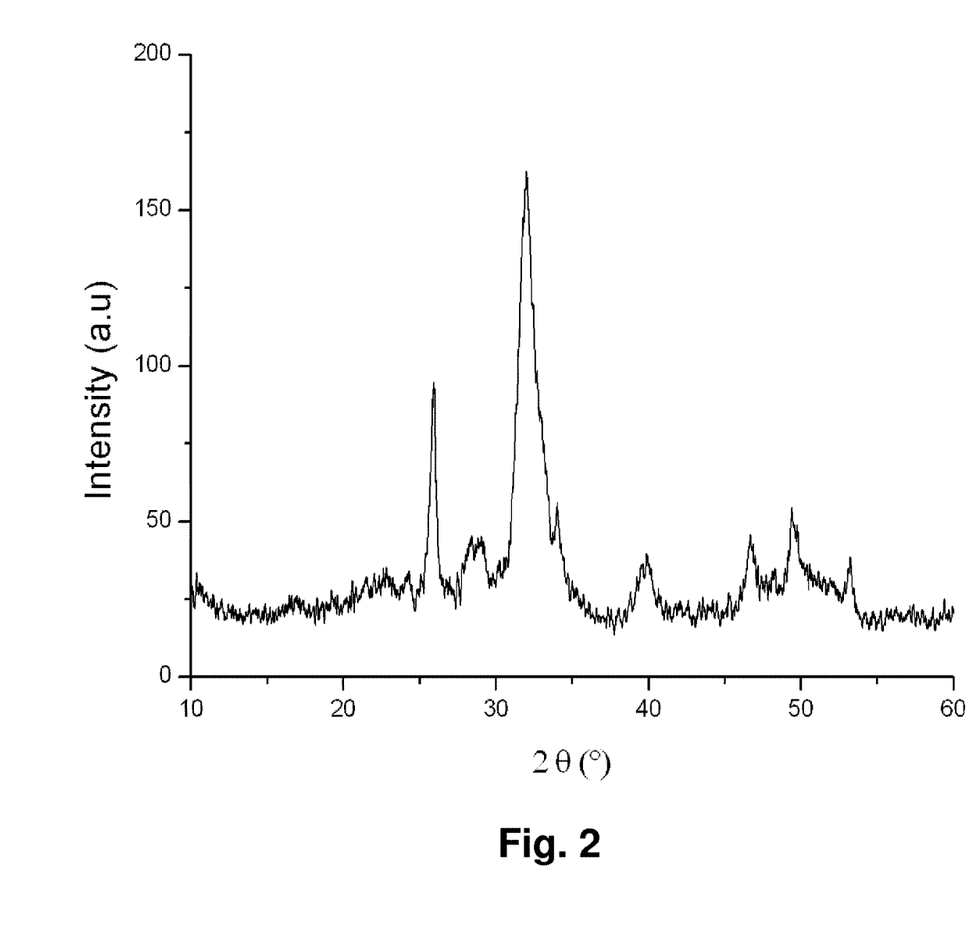
FIG. 2 shows an X-ray diffractogram of heat treated nanocrystalline HA powder. As seen in the Figure, there is a considerable peak broadening due to the small particle size.

B) The crystals were washed extensively with a H$_2$O-isopropanol mixture and dried at 120° C. for 12 hours. The crystals were then heated in an oven at 400° C. for 5 hours in order to remove organic compounds. The specific surface area, as measured with a Micromeritics TriStar instrument using the BET algorithm, was 180 m$^2$/g. The powder was analyzed with a Siemens D5000 powder X-ray diffractometer with CuKα-radiation, and the diffractogram is shown in FIG. 2.

Example 2

In another experiment, 11.5 g of 6-amino hexanoic acid was dissolved in 150 ml H$_2$O. 2.82 g of CaO was added to the solution and allowed to stir for 10 minutes. The pH of this solution was 12.0. Solution 2 was prepared by adding 13.2 g of 6-amino hexanoic acid to 150 ml H$_2$O. 3.45 g of H$_3$PO$_4$ was added to this solution, and allowed to stir for 10 minutes. The pH of this solution was 4.70. Solution 1 was mixed with solution 2, and crystallisation resulted. The crystallisation was carried out at ambient temperature, and the pH was measured to 9.53. The crystals were washed, heated to 400° C. and dried according to Example 1B. The specific surface area was 160 m$^2$/g.

Example 3

In another experiment, solution 1 consisted of 2.82 g CaO, 6.70 g L-aspartic acid and 150 ml H$_2$O. The pH of this solution was 10.1. Solution 2 consisted of 3.45 g $H_3PO_4$, 6.65 g L-Lysine and 150 ml $H_2O$. The pH of this solution was 6.46. The solutions were mixed at ambient temperature, and the pH was measured to 8.10. The precipitated crystals were washed with $H_2O$, dried and heated to 400° C. The specific surface area was 159 $m^2/g$.

Example 4

Figure 1:
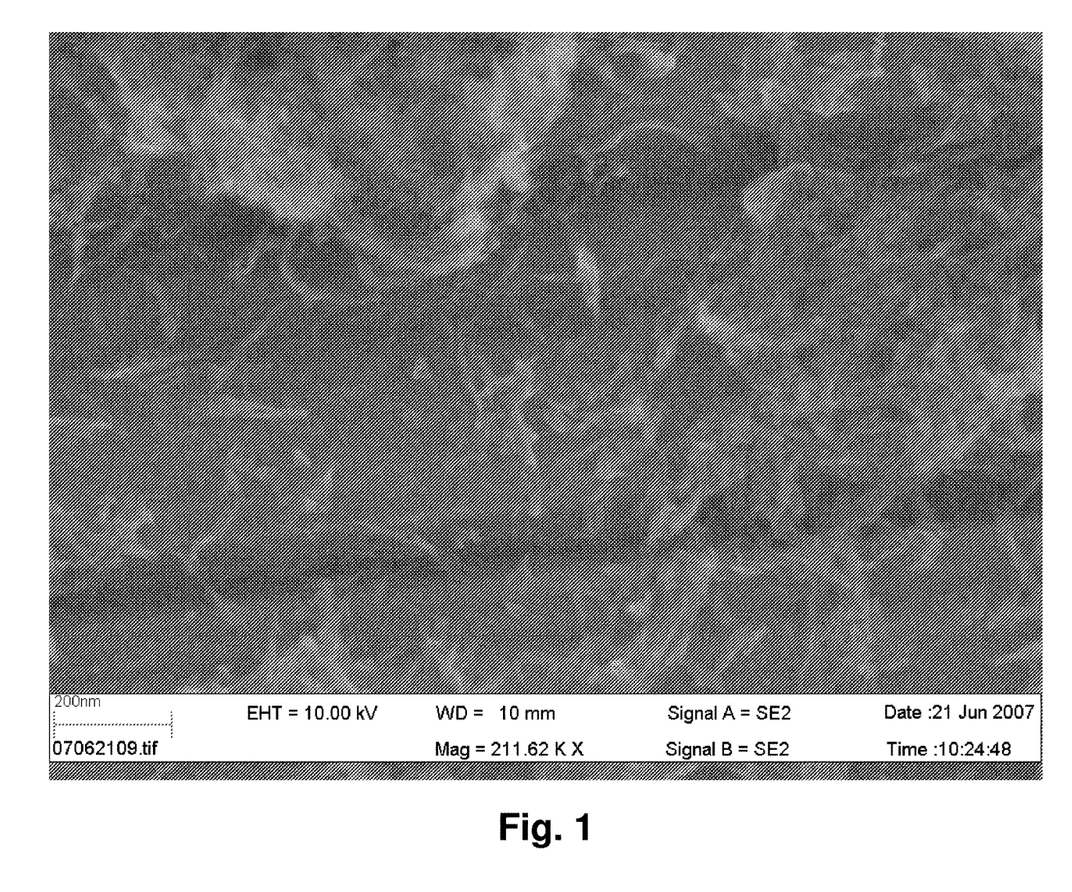
FIG. 1 shows a Scanning Electron Microscope (SEM) image of a titanium surface coated with nanocrystalline HA. Scale bar=200 nm. As seen from this Figure, the HA crystals are needle-shaped, 50-150 nm long and 5-10 nm wide.
Figure 3:
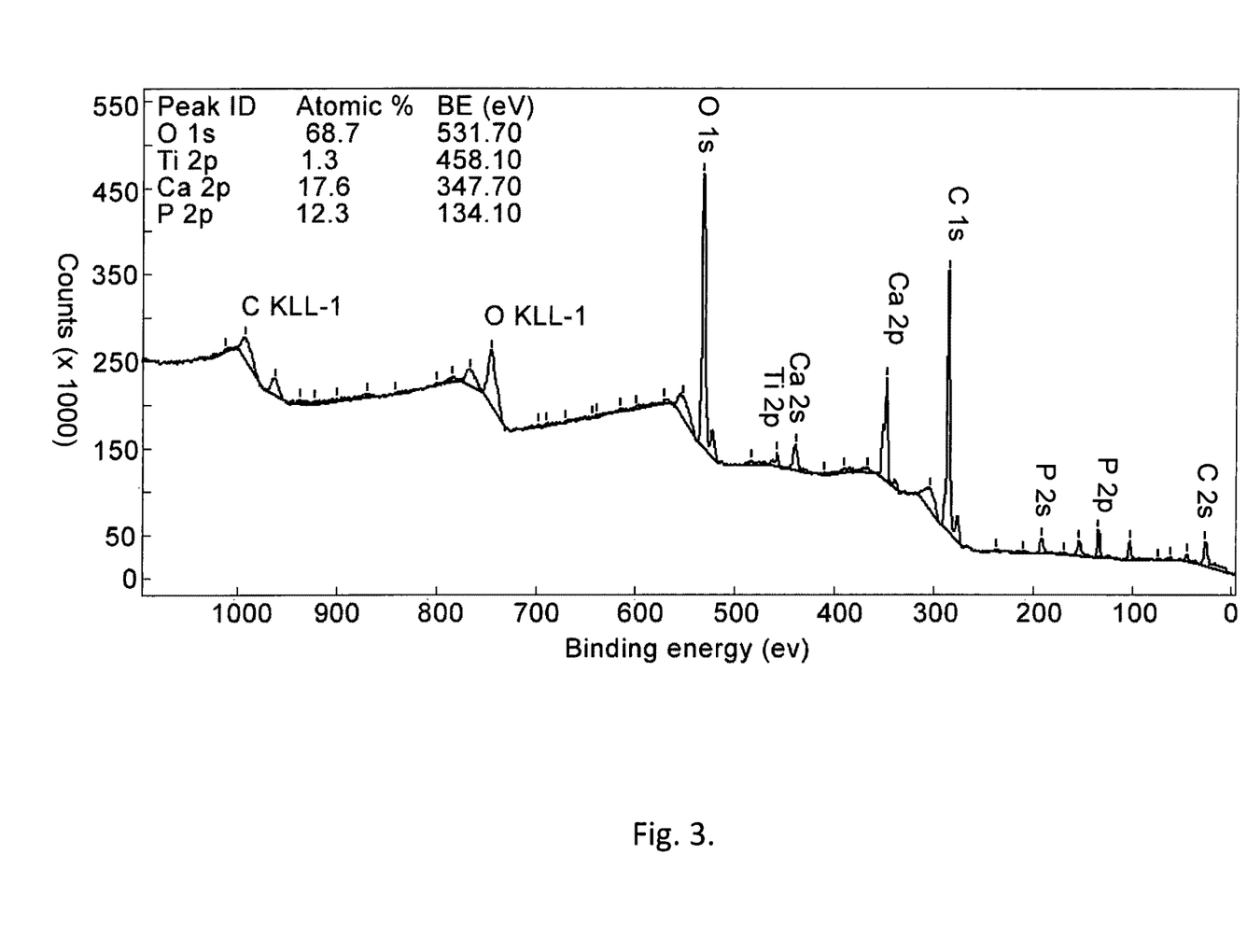
FIG. 3 shows an X-ray Photoelectron Spectroscopy (XPS) spectrum of a titanium surface coated with nanocrystalline HA. As can be seen from this Figure, the titanium content is 1.3%.

In another experiment, the crystals were precipitated according to example 1A. The solution containing nanocrystalline HA particles with the amphoteric GABA molecule attached to the surface of the particles, was used as a coating solution. A titanium disk was dipped into the solution, removed and allowed to dry at room temperature for 1 hour. The disk was then heat treated for 5 minutes in air at 300° C. The disk was allowed to cool to room temperature and washed extensively with water and isopropanol. A crystal layer was visible on the surface of the disk. The titanium disk was analyzed in a LEO ULTRA 55 SEM and a micrograph is shown in FIG. 1. As seen from the figure the crystals on the disk are fibrillar with a length of 50-150 nm, and a diameter of 5-10 nm. EDS measurement revealed a Ca/P ratio of 1.65, close to the theoretical value of natural HA, 1.67. An XPS spectrum, done with a Perkin-Elmer PHI 5000C instrument, of the coated titanium disk is shown in FIG. 3. As seen from this figure, the amount of titanium is 1.3%, which indicates an almost complete HA crystal coverage of the disk.

Example 5

Figure 4:
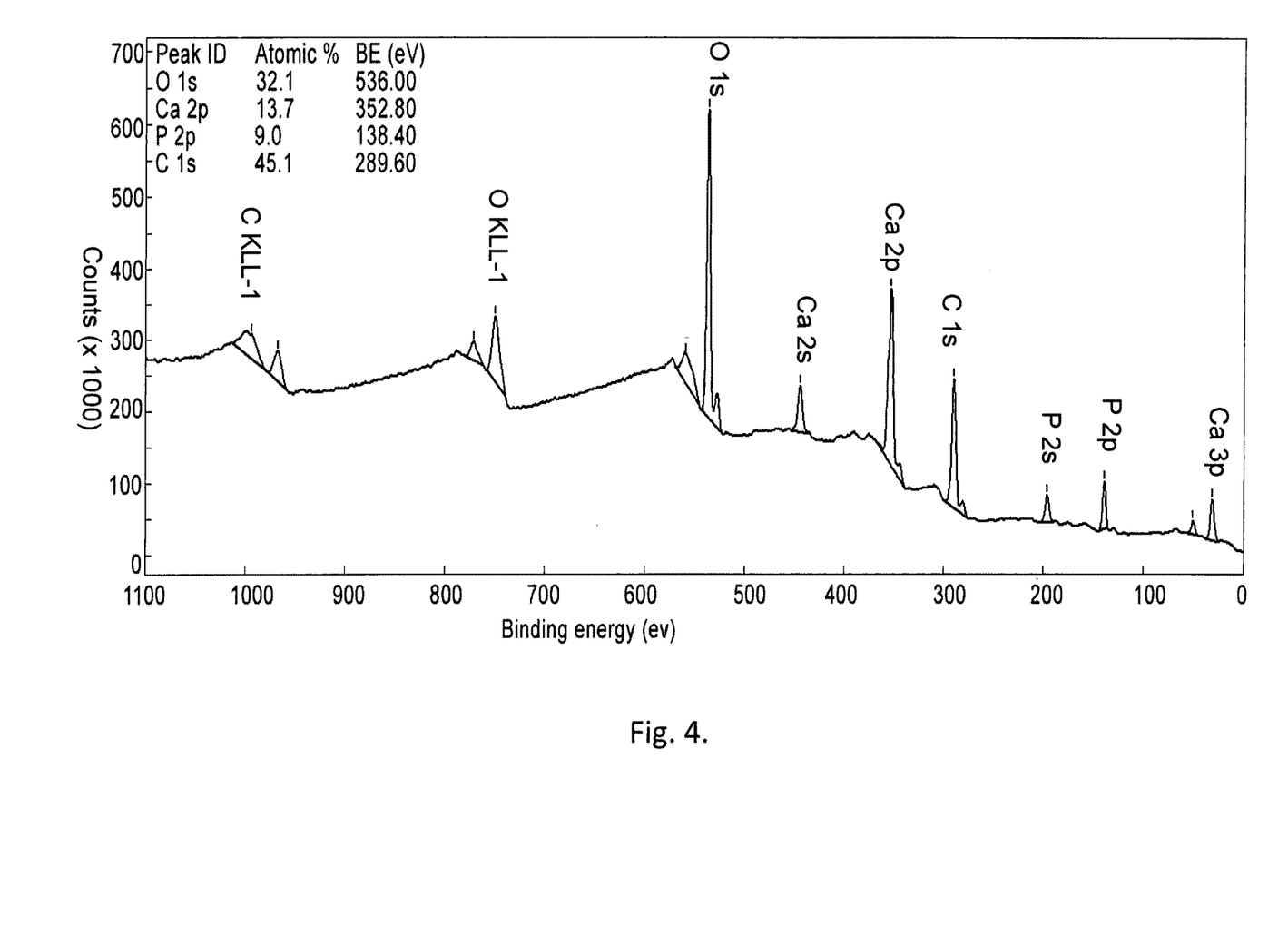
FIG. 4 shows an X-ray Photoelectron Spectroscopy (XPS) spectrum of a poly(styrene) disk coated with coated calcium phosphate particles.

In another experiment, the crystals were precipitated according to example 1A. The solution containing nanocrystalline HA particles with the amphoteric GABA molecule attached to the surface of the particles, was used as a coating solution. A poly(styrene) disk was dipped into the solution, removed and allowed to dry at 80° C. for 1 hour. The disk was then washed extensively with water. A crystal layer was visible on the surface of the disk. The disk was analysed with a Perkin-Elmer PHI 5000C instrument, and the result from this measurement is shown in FIG. 4. As seen from this Figure, the calcium and phosphor content is 13.7 and 9.0%, respectively.

REFERENCES

1. Reis R and Weiner S, Learning From Nature How to Design New Implantable Biomaterials, Kluwer Academic Publishers, London, 90-92 (2004).
2. Lowenstam H A and Weiner S, On biomineralization, Oxford University Press, New York (1989).
3. Guo et al, J. Biomed. Mater. Res. A, DOI 10.1002/jbm.a.31200
4. Wei J et al, Compos. Part B. Eng., 38, 3, 301-305 (2007); Ramay H R R and Zhang M, Biomaterials 25, 21, 5171-5180 (2004).
5. Mullin J W, Crystallization, Elsevier Butterworth-Heinemann, Oxford, 320-325 (2001).
6. Ying J et al, USRE 39196E; Senna M et al, U.S. Pat. No. 6,592,989 B1.
7. Wang A et al, Mater. Lett. 61, 10, 2084-2088 (2007).
8. Kuriakose T A et al, J. Cryst. Growth 263, 1-4, 517-523 (2004).
9. Koumoulidis G C et al, J. Colloid Interf. Sci. 259 2, 254-260 (2003).
10. Bose S and Kumar Saha S K, Chem. Mater., 15, 4464-4469 (2003).
11. Kjellin P and Andersson M, EP 1781568; Uota M. et al, Langmuir 21, 10, 4724-4728 (2005).
12. Uota M et al, Langmuir 21, 10, 4724-4728 (2005).
13. Story B, Burgess A, U.S. Pat. No. 5,730,598
14. Sun L et al, J. Biomed. Mater. Res. A, 58, 5, 570-592 (2001).
15. Wei-Qi Yan et al, Biomaterials, 18, 17, 1185-1190 (1997).
16. Nishimura I et. al, CA 2563 299.
17. Stupp S I et al, US 2004/0258726A1.
18. Gonzalez-Mcquire R et al, J. Mater. Chem., 14, 2277-2281 (2004).
19. Hidalgo-Álvarez R et al, Adv. Colloid Interface Sci., 67, 1-118 (1996).
20. Weidenhammer P and Jacobasch H-J, J. Colloid Interf. Sci., 180, 232-236 (1996).

The invention claimed is:

1. A calcium phosphate particle comprising a water-soluble amino acid, said water-soluble amino acid comprising at least two functional groups comprising a negatively charged group and a positively charged group,
   wherein said negatively charged group of said water-soluble amino acid is attached to said calcium phosphate particle, thereby providing a coated calcium phosphate particle, and
   said positively charged group of said water-soluble amino acid is attached to a solid support comprising an oxide surface or a polymer surface so that said water-soluble amino acid is simultaneously attached to said solid support and said calcium phosphate particle, thereby providing said coated calcium phosphate particle in the form of a coating on said solid support.

2. The calcium phosphate particle of claim 1, wherein the particle is in crystalline form.

3. The calcium phosphate particle of claim 2, wherein the negatively charged group is selected from the group consisting of —COOH, —OPO$_3$H$_2$ and —OSO$_3$H groups and the positively charged group is an amine group.

4. The calcium phosphate particle of claim 2, wherein the calcium phosphate particle is hydroxyapatite.

5. The calcium phosphate particle of claim 2, wherein the water-soluble amino acid is selected from the group consisting of water-soluble amino acids with three functional groups.

6. The calcium phosphate particle of claim 2, wherein the water-soluble amino acid is selected from the group consisting of neutral amino acids, basic amino acids and acidic amino acids.

7. The calcium phosphate particle of claim 1, wherein the negatively charged group is selected from the group consisting of —COOH, —OPO$_3$H$_2$ and —OSO$_3$H groups and the positively charged group is an amine group.

8. The calcium phosphate particle of claim 1, wherein the calcium phosphate particle is hydroxyapatite.

9. The calcium phosphate particle of claim 1, wherein the water-soluble amino acid is selected from the group consisting of water-soluble amino acids with three functional groups.

10. The calcium phosphate particle of claim 1, wherein the water-soluble amino acid is selected from the group consisting of neutral amino acids, basic amino acids and acidic amino acids.

11. The calcium phosphate particle of claim 1, wherein the water-soluble amino acid is aspartic acid or lysine.

12. A calcium phosphate particle comprising a water-soluble amino acid,
   wherein said water-soluble amino acid is monomeric and comprises at least two functional groups comprising a negatively charged group and a positively charged group,
   wherein said negatively charged group of said water-soluble amino acid is attached to said calcium phosphate particle, thereby providing a coated calcium phosphate particle, and
   wherein said positively charged group of said water-soluble amino acid is attached to a solid support comprising an oxide surface or a polymer surface, thereby providing said coated calcium phosphate particle in the form of a coating on said solid support.

* * * * *